US00PP23849P2

(12) United States Plant Patent
van Zoest

(10) Patent No.: US PP23,849 P2
(45) Date of Patent: Aug. 27, 2013

(54) ***CLEMATIS* PLANT NAMED 'ZOMOA'**

(50) Latin Name: ***Clematis* hybrid**
Varietal Denomination: Zomoa

(75) Inventor: Jan van Zoest, Boskoop (NL)

(73) Assignee: J. Van Zoest Beheer B.V., Boskoop (NL)

( * ) Notice: Subject to any disclaimer, the term of this patent is extended or adjusted under 35 U.S.C. 154(b) by 68 days.

(21) Appl. No.: 13/385,268

(22) Filed: Feb. 10, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Penny J. Aguirre

(57) ABSTRACT

A new cultivar of hybrid *Clematis*, 'Zomoa', characterized by its upright facing upright flower that is dark violet-blue in color, its blooms in spring and in summer, its very dark colored, prominent ovate-shaped flower buds, its climbing growth habit, its near sterility, and its cold hardiness to at least U.S.D.A. Zone 6.

2 Drawing Sheets

Botanical classification: *Clematis* hybrid.
Variety denomination: 'Zomoa'.

BACKGROUND OF THE INVENTION

The present invention relates to a new and distinct cultivar of *Clematis* of hybrid origin (Patens Group) and will be referred to hereafter by its cultivar name 'Zomoa'. 'Zomoa' is grown as an herbaceous perennial for landscape use or as a flowering potted plant for the terrace.

'Zomoa' derived from an ongoing breeding program by the Inventor at his nursery in Boskoop, The Netherlands. 'Zomoa' arose as a seedling derived from open pollination of an unnamed plant from the breeding program, designated as No. 19960250. 'Zomoa' was selected as a single unique plant from the batch of seedlings in 2004.

Asexual reproduction of the new cultivar was first accomplished by internodial stem cuttings by the Inventor in Boskoop, The Netherlands in 2004. The characteristics of this cultivar have been determined to be stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zomoa' from other varieties of *Clematis* known to the Inventor.

1. 'Zomoa' exhibits an upright flower that is dark violet-blue in color.
2. 'Zomoa' blooms in spring and in summer.
3. 'Zomoa' exhibits very dark colored, prominent ovate-shaped flower buds.
4. 'Zomoa' exhibits a climbing growth habit.
5. 'Zomoa' is nearly sterile; seed is rarely produced.
6. 'Zomoa' is cold hardy at least to U.S.D.A. Zone 6.

The new cultivar primarily differs from its seed plant by having a much more floriferous habitus and in having larger flowers that are darker in color. 'Zomoa' can be compared to the cultivars 'Sano-no-murasaki' (not patented) and 'The President' (not patented). 'Zomoa' exhibits filaments that are violet in color and flower buds that are ovate in shape and dark violet in color, whereas 'Sano-no-murasaki' exhibits filaments that are purple with a white base in color and flower buds that are lanceolate in shape and greenish in color. 'The President' differs from 'Zomoa' in having filaments that are white in color with a purple tip and violet base and flower buds that are lanceolate in shape and purple in color.

DESCRIPTION OF THE DRAWINGS

The accompanying colored photographs illustrate the overall appearance and distinct characteristics of the new *Clematis*. The photographs were taken of a plant three years in age as grown in a one-gallon container in Boskoop, The Netherlands.

The photograph in FIG. 1 shows the flowering habitus with leaves, flowers and flower buds.

Figure 1:
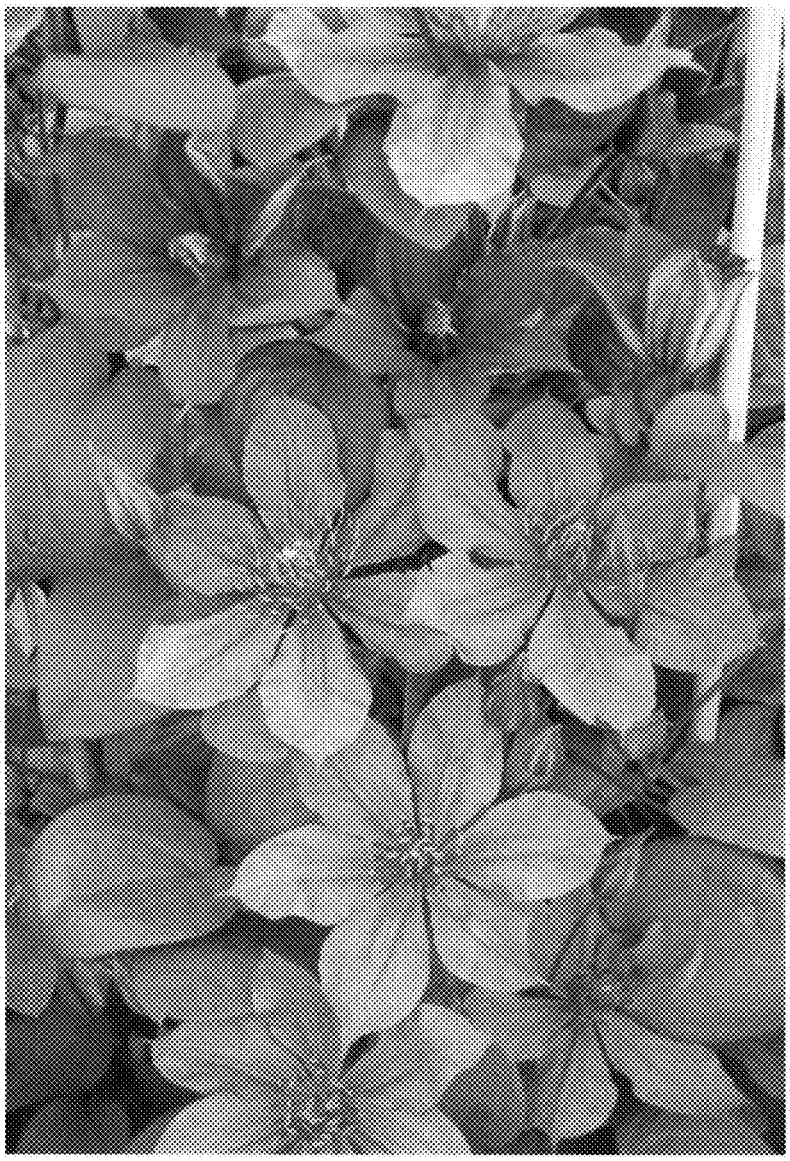
Figure 2:
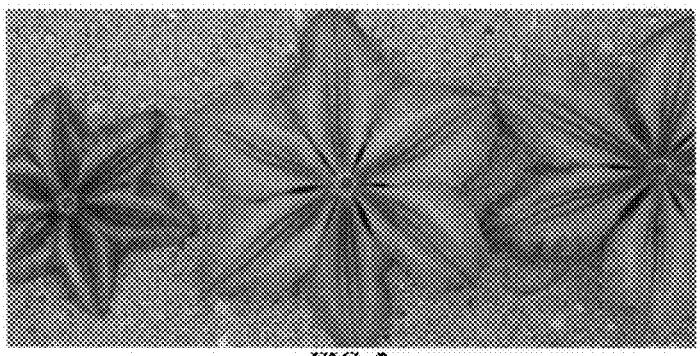

The photograph in FIG. 2 shows the back of the flower.

Figure 3:
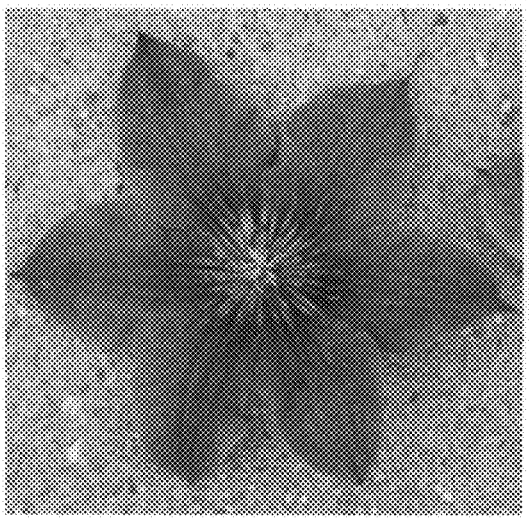

The photograph in FIG. 3 shows the inside of the flower with a close up of the stamens and pistils.

Figure 4:
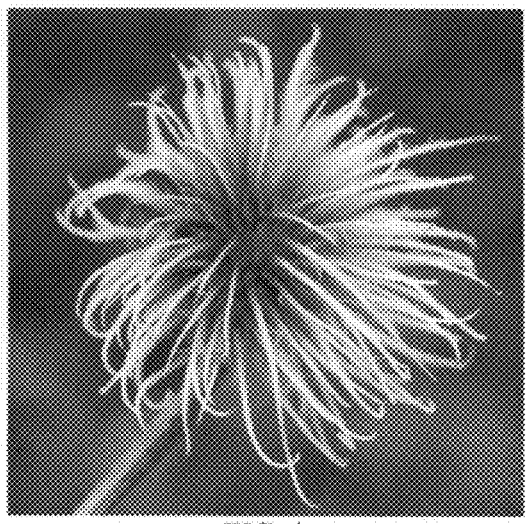

The photograph in FIG. 4 shows the seedhead.

Figure 5:
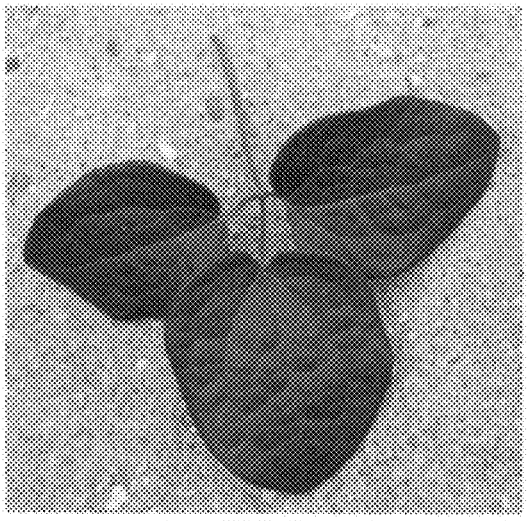
Figure 6:
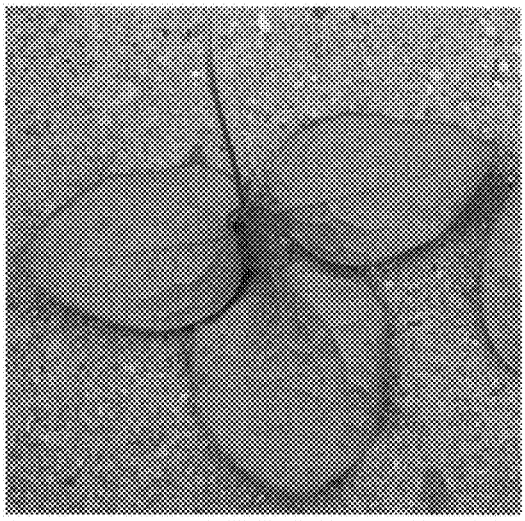

The photograph in FIG. 5 shows the upper surface of a leaf and the photograph in FIG. 6 shows the lower surface of a leaf. The colors of the photographs are as close as possible with the digital photography techniques available, the color values cited in the detailed botanical description describe the colors as accurately as possible of the new *Clematis*.

DETAILED BOTANICAL DESCRIPTION

The following is a detailed description of three year-old plants of *Clematis* 'Zomoa' as grown outdoors in one-gallon containers under full sun at a nursery in Boskoop, The Netherlands. The phenotype of the new cultivar may vary with variations in environmental, climatic and cultural conditions, as the cultivar has not been tested under all possible environmental conditions. The color determination is in accordance with The 2001 R.H.S. Color Chart, London, England, except where general color terms of ordinary dictionary significance are used.

General description:

*Botanical classification.*—*Clematis* 'Zomoa' (classified in the Patens Group).

*Blooming period.*—Blooms for 4 to 6 weeks in spring and for 6 to 8 weeks in summer.

*Plant habit.*—Herbaceous climber.

*Height and spread.*—Three year-old plant is about 15 cm in width at base with a height of about 2 m when pruned after first flowering.

*Cold hardiness.*—At least to U.S.D.A. Zone 6.

*Culture.*—Moist but well-drained soil in full sun with the roots shaded.

*Diseases.*—No resistance to wilt has been observed.

*Root description.*—Fleshy.

Growth and propagation:

*Propagation.*—Internodial soft wood cuttings from vegetative shoots.

*Root initiation.*—Roots develop in 6 to 8 weeks in summer under greenhouse conditions.

*Time required for root development.*—75 to 90 days to develop a 5-cm container from a 5-cm cutting.

*Growth rate.*—Moderate growth once planted out in the landscape.

Stem description:

*Shape.*—Round and 6-ribbed.

*Stem color.*—59A to 59B.

*Stem size.*—About 2 m (including peduncle and terminal pedicel) in length, an average of 2 to 4 mm in diameter.

*Stem surface.*—Covered with sparse grey hairs.

*Internode length.*—Ranges from 5 to 13 cm.

*Branching.*—Basal branches.

Foliage description:

*Leaf arrangement.*—Opposite.

*Leaf division.*—Ternate but upper leaves in the inflorescence simple.

*Leaf size.*—Up to 13 cm in length and 12 cm in width.

*Leaf Attachment.*—Petiolate.

*Leaflet shape.*—Ovate.

*Leaflet base.*—Obtuse on terminal leaflet, oblique on the side leaflets.

*Leaflet apex.*—Acute.

*Leaflet fragrance.*—Rather strong, smelly fragrance when crushed.

*Leaflet venation.*—Slightly reticulate at upper surface, lower surface more prominently reticulate with thick main veins, color on upper and lower surface; 144A.

*Leaflet margins.*—Entire on ternate leaves, on simple leaves sometimes with a lobe.

*Leaflet attachment.*—Petiolulate.

*Leaflet surface.*—Upper surface glabrous with a few very short hairs on main veins, lower surface sparsely hairy with long hairs especially on main veins.

*Leaflet size.*—Up to 6 cm in length and 5 cm in width.

*Leaflet color.*—Upper surface 147A, lower surface 146B.

*Petioles and petiolules.*—Petiole; 3 to 8 cm in length and about 2 mm in width, thick articulate on simple leaves towards leaflet, 59A in color, surface is sparsely hairy, petiolule; 1 to 2 cm in length and about 1 mm in width, color 144A flushed with 59A, surface is sparsely hairy.

Inflorescence description:

*Inflorescence type.*—3-5-7-flowered dichasial cyme.

*Inflorescence arrangement.*—Terminal and axillary on young shoots.

*Peduncles.*—Up to 10 cm in length and about 3 mm in width, round and slightly 6-ribbed, surface is sparsely hairy, 59C in color.

*Pedicels.*—Up to 8 cm in length and about 2 mm in width, round and slightly 6 ribbed, surface is sparsely hairy but more densely so towards flower, 144B in color with dark 59A ribs.

*Flower bud description.*—Up to 3 cm in length at opening, ovate in shape, apex acute, base obtuse, sparsely hairy but more densely so at the seams, 79A in color.

*Flower fragrance.*—Very faint.

*Lastingness of the flowers.*—Individual flowers last about 10 to 14 days until the first tepal drop followed later by the stamens.

*Flower quantity.*—Flowers terminal and axillary on young shoots, about 20 to 30 flowers in spring and about 50 flowers in summer on a 3 year-old plant.

*Flower type.*—Single, spreading, star-shaped.

*Flower aspect.*—Upright facing.

*Flower size.*—Range from 7 to 12 cm in diameter, about 2.5 cm in depth.

*Flower sex.*—Bisexual.

*Tepal number.*—6.

*Tepal shape.*—Broadly elliptic.

*Tepal apex.*—Acute to abruptly acute with needle-like tip.

*Tepal base.*—Cuneate.

*Tepal margin.*—Entire.

*Tepal surface.*—Upper surface; glabrous, lower surface; glabrous with a few hairs on the main veins, margin glabrous to short villous near middle.

*Tepal color.*—Upper surface; very dark velvet, N92A at the base, N89A in the center region, veins and margins N89A, fading to N89C to N89D with small base 155B, lower surface; 86B in the center, veins N92A, margins 86A, 92B between the center and margin.

*Tepal size.*—Up to 6 cm in length and 3 cm in width.

Reproductive organs:

*Gynoecium.*—Numerous pistils (up to 40), 1.5 to 2 cm in length, style; 161D and hairy on lower half, upper half glabrous and 11C in color, ovary; 145C in color with hairy surface; stigma; 158B in color, not thickened and slightly refluxed.

*Androcoecium.*—Filaments are 0.6 to 1.5 cm in length, 0.1 cm in width at the base and 0.15 cm in width near anthers, oblanceolate in shape, 86C to 86D in color (darkest towards anthers), anthers; 0.4 cm in length, linear, 59A in color with pollen 201C in color; connective N79B in color, glabrous but sometimes a few hairs, not elongated, becoming 202A in color.

*Seed.*—Usually no fertile seed is produced, head; up to 4 cm in diameter, ovary; shiny 145C in color, style up to 2 cm in length with hairs 161D in color; stigma 158B in color.

It is claimed:

1. A new and distinct cultivar of *Clematis* plant named 'Zomoa' as herein illustrated and described.

* * * * *